United States Patent
Ohashi

(10) Patent No.: US 9,976,998 B2
(45) Date of Patent: May 22, 2018

(54) SYSTEM AND METHOD FOR CONTROLLING LIQUID CHROMATOGRAPH

(71) Applicant: SHIMADZU CORPORATION, Kyoto-shi, Kyoto (JP)

(72) Inventor: Hiroshi Ohashi, Otsu (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 402 days.

(21) Appl. No.: 14/328,926

(22) Filed: Jul. 11, 2014

(65) Prior Publication Data

US 2015/0019141 A1    Jan. 15, 2015

(30) Foreign Application Priority Data

Jul. 12, 2013    (JP) .................................. 2013-146066

(51) Int. Cl.
*G01N 30/28*    (2006.01)
*G01N 30/86*    (2006.01)
(Continued)

(52) U.S. Cl.
CPC ......... *G01N 30/8658* (2013.01); *B01D 15/08* (2013.01); *G01N 30/34* (2013.01); *G01N 30/466* (2013.01)

(58) Field of Classification Search
CPC ...... B01D 15/203; B01D 15/20; G01N 30/86; G01N 30/8696; G01N 30/8693;
(Continued)

(56) References Cited

U.S. PATENT DOCUMENTS 3,721,813 A * 3/1973 Condon et al. .... G01N 30/8675
   702/1
4,969,993 A * 11/1990 Nash, Jr. ................. G01N 30/24
   210/143
(Continued)

FOREIGN PATENT DOCUMENTS

JP    2005-127814 A    5/2005
JP    2013-24601 A    2/2013
WO    2013/011818    12/2013

OTHER PUBLICATIONS

Chinese Office Action dated Jul. 13, 2015 in Chinese Patent Application No. 201410332487.3.
(Continued)

*Primary Examiner* — Katherine Zalasky
(74) *Attorney, Agent, or Firm* — Sughrue Mion, PLLC

(57) ABSTRACT

Provided is a liquid chromatograph control system for controlling an operation of a liquid chromatograph according to a method file containing a plurality of analysis parameters representing configuration items which determine operational conditions of the liquid chromatograph, including: a) a display section for displaying, for each of the analysis parameters, selectable values of the analysis parameter on a condition-setting screen; b) a grouping section for allowing a user to prepare grouping information for the values of the analysis parameter displayed on the condition-setting screen, the grouping information determining whether or not one value of one analysis parameter and one value of another analysis parameter can be included in one group; and c) a file-creating section for extracting, from the values of the analysis parameters, such values that can be included in one group according to the grouping information, and for creating a method file containing the extracted values.

4 Claims, 5 Drawing Sheets

(51) Int. Cl.
*G01N 30/88* (2006.01)
*B01D 15/08* (2006.01)
*B01D 15/16* (2006.01)
*G01N 30/34* (2006.01)
*G01N 30/46* (2006.01)

(58) Field of Classification Search
CPC .......... G01N 30/8651; G01N 30/8658; G01N 30/50; G01N 30/88; G01N 30/25; G01N 2030/88988; G01N 30/8804; G01N 2030/889; G01N 2030/8809; G01N 2030/8804
See application file for complete search history.

(56) References Cited

U.S. PATENT DOCUMENTS

| | | | | |
|---|---|---|---|---|
| 7,962,893 | B2* | 6/2011 | Tatsumi | G01N 30/24 717/106 |
| 2002/0098595 | A1* | 7/2002 | Lubman | C07K 1/36 436/178 |
| 2002/0199094 | A1* | 12/2002 | Strand | B01J 19/0093 713/150 |
| 2003/0068828 | A1* | 4/2003 | Dadala | B01J 19/008 436/161 |
| 2003/0229451 | A1* | 12/2003 | Hamilton | G01N 30/8655 702/19 |
| 2004/0126437 | A1* | 7/2004 | Ribeiro | G01N 30/88 424/725 |
| 2004/0172200 | A1* | 9/2004 | Kearney | H01J 49/0027 702/19 |
| 2005/0193262 | A1* | 9/2005 | Osaka | G01N 35/00871 714/37 |
| 2006/0048846 | A1* | 3/2006 | Roenneburg | G01N 30/88 141/130 |
| 2006/0167661 | A1* | 7/2006 | Fukuya | G01N 30/88 702/185 |
| 2007/0005254 | A1* | 1/2007 | Nilsson | G01N 30/8651 702/19 |
| 2007/0288217 | A1* | 12/2007 | Dadala | G01N 30/8651 703/12 |
| 2007/0299633 | A1* | 12/2007 | Ohsaka | G06Q 10/10 702/188 |
| 2008/0052672 | A1* | 2/2008 | Tatsumi | G01N 30/24 717/114 |
| 2009/0179147 | A1* | 7/2009 | Milgram | G01N 30/8651 250/282 |
| 2010/0250147 | A1* | 9/2010 | Verseput | G06Q 10/00 702/32 |
| 2010/0252502 | A1* | 10/2010 | Witt | F04B 11/0058 210/656 |
| 2013/0018598 | A1* | 1/2013 | Ohashi | G01N 30/34 702/25 |
| 2013/0085674 | A1* | 4/2013 | Zhdaneev | E21B 49/10 702/6 |
| 2013/0295597 | A1* | 11/2013 | DeWitte | G01N 30/06 435/23 |
| 2013/0303409 | A1* | 11/2013 | Kapps | G01N 30/24 506/39 |
| 2013/0316462 | A1* | 11/2013 | Bruton, Jr. | G01N 33/92 436/71 |

OTHER PUBLICATIONS

Baidu-Wenku, "Efficient management system for a liquid chromatograph", Sep. 22, 2011.
Communication dated Sep. 6, 2016 from the Japanese Patent Office in corresponding application No. 2013-146066.

* cited by examiner

Fig. 5A

| No. | COMBINATION OF THE VALUES OF ANALYSIS PARAMETERS OF SOLVENT A AND SOLVENT B | | APPROPRIATE-NESS |
|---|---|---|---|
| | SOLVENT A | SOLVENT B | |
| 1 | TFA / WATER | TFA / ACN | APPROPRIATE |
| 2 | TFA / WATER | $CH_3COONH_4$ / ACN | INAPPROPRIATE |
| 3 | $CH_3COONH_4$ / WATER | TFA / ACN | INAPPROPRIATE |
| 4 | $CH_3COONH_4$ / WATER | $CH_3COONH_4$ / ACN | APPROPRIATE |

Fig. 5B

| ANALYSIS PARAMETER OF SOLVENT A | GROUP NUMBER |
|---|---|
| TFA / WATER | 1 |
| $CH_3COONH_4$ / WATER | 2 |

| ANALYSIS PARAMETER OF SOLVENT B | GROUP NUMBER |
|---|---|
| TFA / ACN | 1 |
| $CH_3COONH_4$ / ACN | 2 |

Fig. 6A

| METHOD FILE NAME | MOBILE PHASE ※ | | GRADIENT PROFILE | COLUMN | ... |
|---|---|---|---|---|---|
| FILE 1 | TFA / WATER (1) | TFA / ACN (1) | G1 | C1 | ... |
| FILE 2 | $CH_3COONH_4$ / WATER (2) | $CH_3COONH_4$ / ACN (2) | G1 | C1 | ... |

※ THE NUMBERS IN PARENTHESES DENOTE GROUP NUMBERS.

Fig. 6B

| METHOD FILE NAME | MOBILE PHASE | | GRADIENT PROFILE | COLUMN | ... |
|---|---|---|---|---|---|
| FILE 1 | TFA / WATER | TFA / ACN | G1 | C1 | ... |
| FILE 2 | TFA / WATER | $CH_3COONH_4$ / ACN | G1 | C1 | ... |
| FILE 3 | $CH_3COONH_4$ / WATER | TFA / ACN | G1 | C1 | ... |
| FILE 4 | $CH_3COONH_4$ / WATER | $CH_3COONH_4$ / ACN | G1 | C1 | ... |

| ANALYSIS NUMBER | SAMPLE NAME | AMOUNT OF INJECTION | METHOD FILE NAME | DATA FILE NAME | ... |
|---|---|---|---|---|---|
| 1 | SAMPLE 1 | 10 | FILE 1 | DATA 1 | ... |
| 2 | SAMPLE 2 | 10 | FILE 2 | DATA 2 | ... |
| 3 | SAMPLE 3 | 10 | FILE 3 | DATA 3 | ... |
| ⋮ | ⋮ | ⋮ | ⋮ | ⋮ | |
FIG. 7
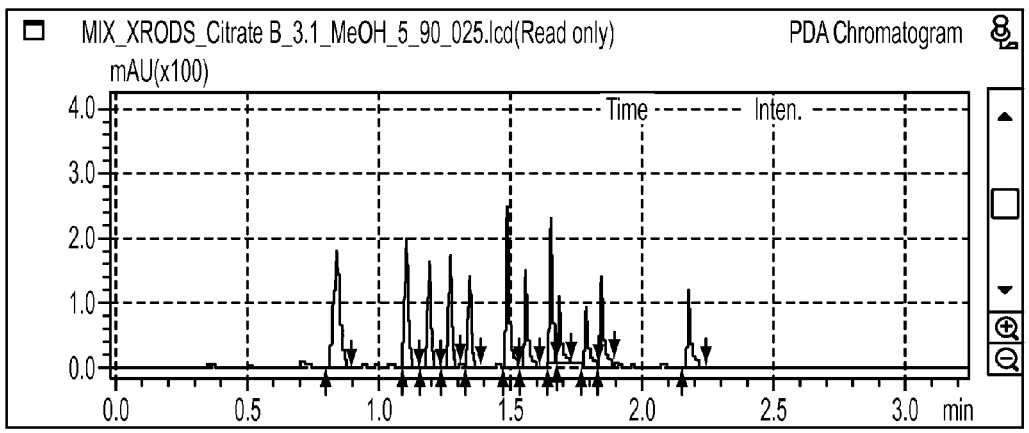
FIG. 8A
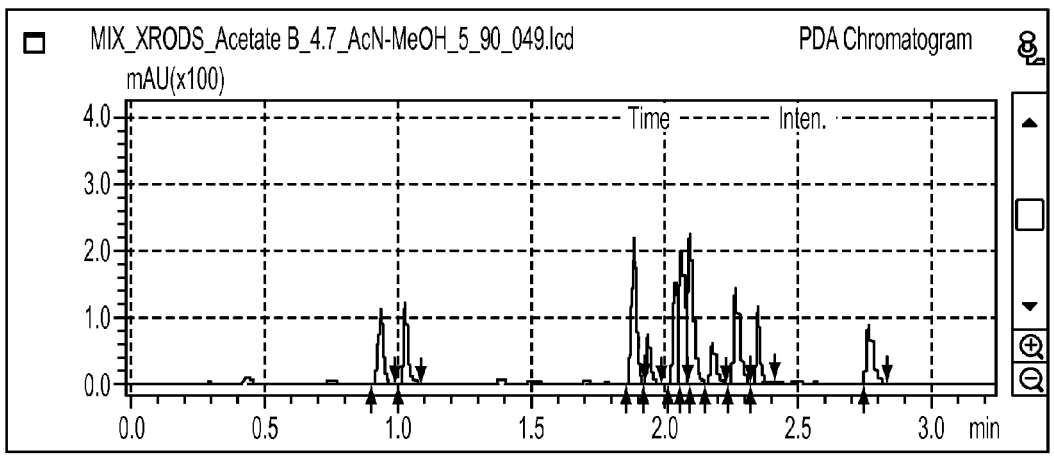
FIG. 8B

US 9,976,998 B2

SYSTEM AND METHOD FOR CONTROLLING LIQUID CHROMATOGRAPH

TECHNICAL FIELD

The present invention relates to a control system for a liquid chromatographic analysis having the function of setting parameters related to analysis conditions, as well as a method to be used in such a system. Specifically, it relates to a system and method for preparing a method file containing a combination of two or more analysis parameters.

BACKGROUND ART

A liquid chromatograph is composed of a plurality of units, such as a pump, a liquid injector and a column oven. The operation of each unit is controlled according to control signals fed from a control system.

In recent years, in such a liquid chromatograph, a control system consisting of a computer having a predetermined controlling and processing program installed have been widely used in order to comprehensively control each analysis unit and process collected data. In such a control system, a continuous analysis of a number of samples or similar operation can be automatically performed by using a schedule table prepared in advance of the analysis (for example, see Patent Literature 1).

FIG. 7 shows one example of the schedule table used in a liquid chromatographic analysis. Each row of the table corresponds to one analysis and holds information necessary for performing the analysis, such as the sample number, the amount of sample to be injected, the name of a method file, and the name of a data file in which an analysis result is to be saved. The "method file" is a file in which the values of the parameters that specify operational conditions of each unit in the liquid chromatograph are stored. For example, this file contains analysis parameters which indicate the kinds or values of various configuration items, such as the kind of mobile phase and the kind of column to be used in the analysis, the flow rate of a pump and the temperature of the column oven during the analysis. (A set of analysis parameters used in one analysis is collectively called the "analysis method.")

After the schedule table is prepared, when an order to initiate the analysis is given, an analysis of a number of samples is automatically performed, in which each sample is sequentially selected according to the schedule and the analysis conditions are set according to the analysis method specified in the corresponding method file.

In such a liquid chromatograph, a different analysis method yields a different result. FIGS. 8A and 8B illustrate how the result of an analysis changes when different analysis methods are used. FIGS. 8A and 8B each shows a chromatogram obtained by an analysis of the same sample using a gradient liquid-supply method (such an analysis is hereinafter called the "gradient analysis") in which the proportion of solvent B in the mixed liquid was initially maintained at 90% for five minutes from the injection of the sample and subsequently lowered to 5% over two minutes. In FIG. 8A, solvent A is a 10-mmol/L solution of sodium citrate (pH 3.1) and solvent B is methanol. In FIG. 8B, solvent A is a 10-mmol/L solution of sodium acetate (pH 4.7) and solvent B is a 50:50 mixture of methanol and acetonitrile.

Since the result of an analysis thus changes depending on the analysis method, users need to perform a preliminary analysis for one sample under various conditions and select the most suitable analysis method for the sample based on the obtained results. Such a preliminary process (search) is called the "method scouting."

In the method scouting, the user specifically sets the analysis parameters representing various configuration items, such as the kind of mobile phase, the kind of column, the value of the flow rate of the pump during the analysis, the value of the temperature of the column oven, the value of the composition ratio of the mobile phase (when it is composed of two solvents), and the range over which the composition ratio is changed with time (when a gradient analysis is performed). Subsequently, a number of method files each of which contains a different combination of the values of the analysis parameters within the specified ranges are exhaustively created by the user or the program, and a schedule table including those method files is created. Upon receiving an order to initiate the analysis, the system sequentially performs a plurality of analyses according to the conditions specified in each row of the schedule table. The chromatogram data obtained as a result of each analysis are compiled into one data file and saved in a storage device, such as a hard disk drive. Later on, the user browses through the chromatogram data saved in the storage device and selects, as the analysis method to be used in an actual analysis of the sample, an analysis condition under which the best analysis result has been obtained.

CITATION LIST

Patent Literature

Patent Literature 1: JP 2005-127814 A

SUMMARY OF INVENTION

Technical Problem

As stated earlier, in the method scouting, a number of method files each of which contains a different combination of the values of the analysis parameters are exhaustively created. However, some of those combinations of the values of the analysis parameters are meaningless or inappropriate. For example, the combination of two solvents which respectively contain trifluoroacetic acid (TFA) and acetic acid as pH-control reagents is inappropriate for use as the mobile phase since the effects of the two additives cancel each other. The combination of a solvent containing 0.1% of formic acid and a solvent containing 0.01% of formic acid is meaningless for use as the mobile phase since the formic-acid concentration of the resulting mobile phase changes with time. Furthermore, mixing some kinds of solvents causes deposition of the additives contained in the solvents; such a combination of solvents is also inappropriate for use as the mobile phase.

Performing a preliminary analysis according to a method file which contains a meaningless or inappropriate combination of the values of the analysis parameters causes not only a corresponding increase in the period of time for the preliminary analysis but also a waste of solvent and sample. Furthermore, if the aforementioned deposition occurs, the subsequent analyses will be impeded.

The present invention has been developed to solve the aforementioned problem. Its primary objective is to provide a control system having the function of setting the analysis parameters for a liquid chromatograph, in which inappropriate combinations of the values of the analysis parameters are prevented from being included in the method files prepared for the method scouting.

Solution to Problem

The present invention aimed at solving the previously described problem provides a liquid chromatograph control system for controlling an operation of a liquid chromatograph according to a method file containing a plurality of analysis parameters representing configuration items which determine operational conditions of the liquid chromatograph, the control system including:

a) a display section for displaying, for each of the analysis parameters, selectable values of the analysis parameter on a condition-setting screen;

b) a grouping section for allowing a user to prepare grouping information for the values of the analysis parameter displayed on the condition-setting screen, the grouping information determining whether or not one value of one analysis parameter and one value of another analysis parameter can be included in one group; and c) a file-creating section for extracting, from the values of the analysis parameters, such values that can be included in one group according to the grouping information, and for creating a method file containing the extracted values.

Examples of the configuration items are as follows: In the case where the mobile phase used in a chromatographic analysis is composed of a plurality of different solvents, the composition ratio of those solvents is a configuration item. If a gradient liquid-supply is used, the pattern of the temporal change in the composition ratio is a configuration item. The kind of column may also be included in the configuration items. The analysis parameters hold specific values of the configuration items in the method file (such as the kinds of solvents composing the mobile phase or the kind of column).

The display section displays, for each of the analysis parameters, selectable values of the analysis parameter on a condition-setting screen. The grouping section allows a user to prepare grouping information for the values of the analysis parameter displayed on the condition-setting screen, where the grouping information is a piece of information to be used for determining whether or not one value of one analysis parameter and one value of another analysis parameter can be included in one group. For example, when the natures of the two kinds of mobile phases (e.g. acidic and basic, or organic and water-based) are taken into account, the grouping is performed in such a manner that such kinds of mobile phases that can be appropriately combined (e.g. acetic-acid-based solvents, TFA-based solvents, and so on) will be included in the same group. The combinations of the other analysis parameters, such as the kind of mobile phase and the polarity of the column, may also be similarly taken into account for the grouping. The file-creating section extracts, from the values of the analysis parameters, such values that can be included in one group according to the grouping information, and creates a method file containing the extracted values. As a result, any meaningless or inappropriate combination of the values of the analysis parameters is excluded and the method scouting is efficiently performed.

The present invention also provides a liquid chromatograph control method for controlling an operation of a liquid chromatograph according to a method file containing a plurality of analysis parameters representing configuration items which determine operational conditions of the liquid chromatograph, the control method including:

a) a display step, in which, for each of the analysis parameters, selectable values of the analysis parameter are displayed on a condition-setting screen;

b) a grouping step, in which a user is allowed to prepare grouping information for the values of the analysis parameter displayed on the condition-setting screen, the grouping information determining whether or not one value of one analysis parameter and one value of another analysis parameter can be included in one group; and c) a file-creating step, in which such values that can be included in one group according to the grouping information are extracted from the values of the analysis parameters and a method file containing the extracted values is created.

Advantageous Effects of the Invention

In the liquid chromatograph control system and its control method according to the present invention, the values of the analysis parameters representing the configuration items are grouped based on the grouping information which shows whether or not one value of one analysis parameter and one value of another analysis parameter can be included in one group. A method file is created for only such a combination of the values that belong to the same group. No method file which contains a meaningless or inappropriate combination of the values is created. Therefore, the method scouting can be performed without wasting time, solvents and samples for unnecessary analyses.

BRIEF DESCRIPTION OF DRAWINGS

FIG. 5A is a table showing all combinations of the two values of one analysis parameter (solvent A) and the two values of another analysis parameter (solvent B) entered in the liquid chromatograph control system of the present embodiment, and FIG. 5B is a table showing the group names assigned to each of the values of those analysis parameters.

FIG. 6A is one example of the schedule file created in the method scouting by the system according to the present embodiment, and FIG. 6B is the corresponding example of the schedule file created by a conventional system.

FIG. 7 is one example of the schedule table.

FIGS. 8A and 8B illustrate how the result of an analysis changes when different analysis methods are used.

DESCRIPTION OF EMBODIMENTS

Figure 1:
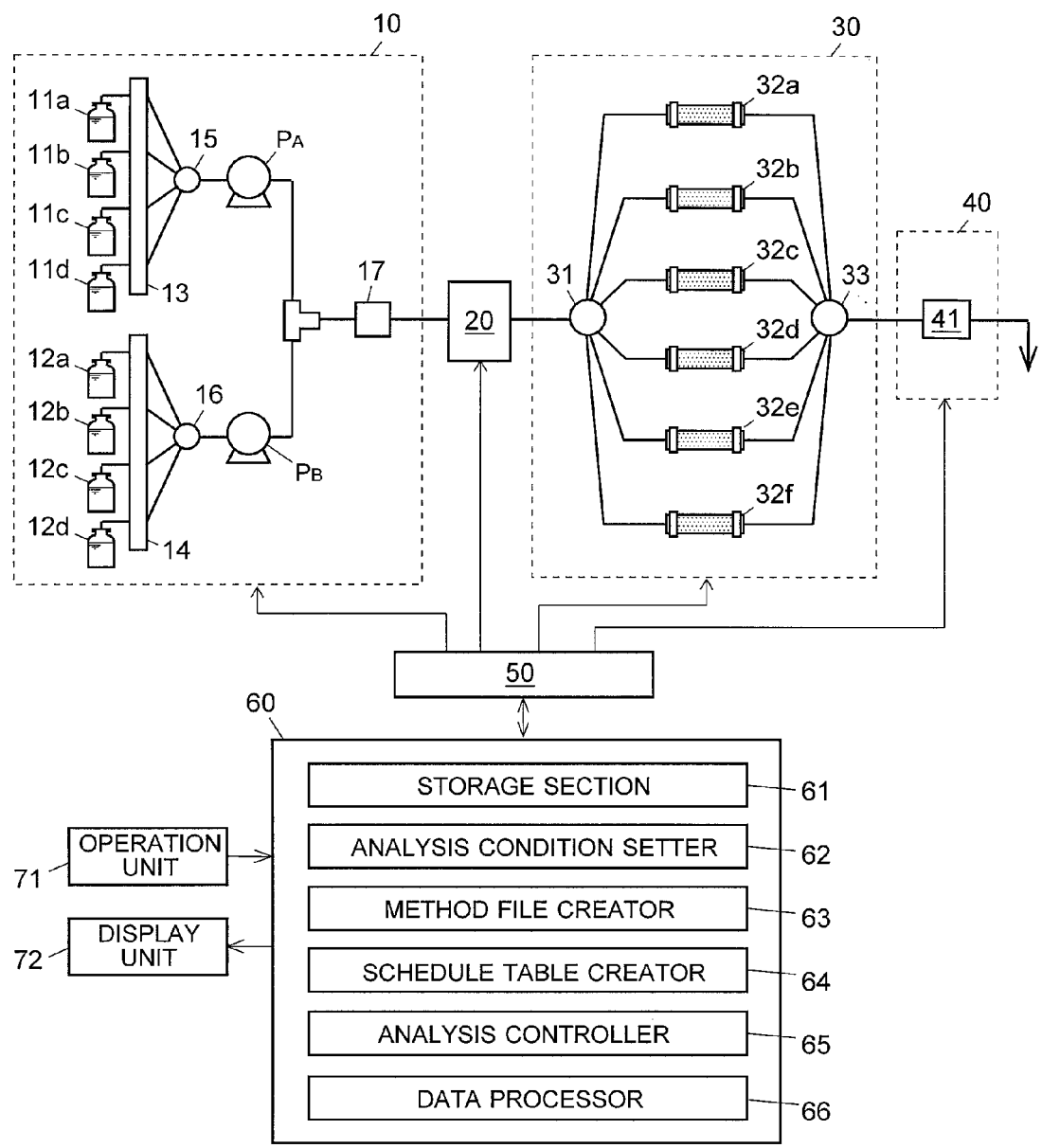
FIG. 1 is a schematic configuration diagram of a liquid chromatograph equipped with a liquid chromatograph control system according to one embodiment of the present invention.

One embodiment of the liquid chromatograph control system according to the present invention is hereinafter described with reference to the attached drawings. FIG. 1 is a schematic configuration diagram of a liquid chromatograph equipped with a liquid chromatograph control system according to the present embodiment. The liquid chromatograph in the present embodiment is capable of a gradient analysis in which a chromatographic analysis is performed while temporally changing the mixture ratio of two solvents (solvents A and B) which composes the mobile phase.

Naturally, the liquid chromatograph control system according to the present invention cannot only be used for a gradient analysis (as in the present embodiment) but also for an "isocratic analysis", i.e. an analysis in which the mobile phase is composed of two solvents but the composition ratio of the two solvents is not changed.

The present liquid chromatograph includes a liquid-sending unit 10, an auto-sampler 20, a column oven 30, a detecting unit 40, a system controller 50 for controlling each of those units, a control system 60 for conducting the analysis task through the system controller 50 and for analyzing and processing data obtained with the detecting unit 40, an operation unit 71 consisting of a keyboard and a mouse connected to the control system 60, a display unit 72 as well as other devices.

The liquid-sending unit 10 is a system for drawing two solvents (labelled "A" and "B") through liquid-sending pumps $P_A$ and $P_B$, respectively, and for supplying the two solvents to a column after mixing them with a gradient mixer 17. Each of the liquid-sending pumps $P_A$ and $P_B$ has four solvent containers connected via a solvent-switching valve 15 or 16 and a deaerator 13 or 14. The solvent containers 11a-11d connected to the liquid-sending pump $P_A$ hold a set of similar solvents, e.g. water-based solvents (solvents whose main component is water). By means of the solvent-switching valve 15, one of the four solvent containers 11a-11d can be selected so that the solvent in the selected container will be drawn by the liquid-sending pump $P_A$ as solvent A. The solvent containers 12a-12d connected to the liquid-sending pump $P_B$ hold another set of similar solvents, e.g. organic solvents (solvents whose main component is an organic solvent). By means of the solvent-switching valve 16, one of the four solvent containers 12a-12d can be selected so that the solvent in the selected container will be drawn by the liquid-sending pump $P_B$ as solvent B. The flow rates of the liquid-sending pumps $P_A$ and $P_B$ can be individually varied with time in a controlled manner, whereby a gradient-mode liquid supply in which the mixture ratio of solvents A and B changes with time is performed. The column oven 30 includes six columns 32a-32f as well as two passage-switching elements 31 and 33 for selectively connecting one of the columns to the passage of the mobile phase. The detecting unit 40 includes a detector 41, such as a photodiode array (PDA) detector.

The control system 60 includes, as its functional blocks, a storage section 61, an analysis condition setter 62, a method file creator 63, a schedule table creator 64, an analysis controller 65 and a data processor 66. The control system 60 is actually a computer with various functions (which will be described later) realized by executing a dedicated controlling and processing software program installed on the computer.

A standard operation of one gradient analysis using the previously described liquid chromatograph is as follows: Under the control of the system controller 50 which has received a command from the analysis controller 65 of the control system 60, each of the solvent-switching valves 15 and 16 is set to select one solvent container and make the solvent in the selected container drawn into the corresponding liquid-sending pump $P_A$ or $P_B$ at a preset flow rate. Solvents A and B which are respectively drawn by the liquid-sending pumps $P_A$ and $P_B$ are uniformly mixed in the gradient mixer 17. The resulting mixture, which serves as the mobile phase, flows through the auto-sampler 20 into a column. The auto-sampler 20, in which a rack holding one or more sample bottles (vials) is set, selects a predetermined sample under the control of the system controller 50, collects a preset volume of the sample and injects it into the mobile phase at a predetermined timing. The injected sample is carried by the mobile phase into one of the columns 32a-32f.

Figure 3:
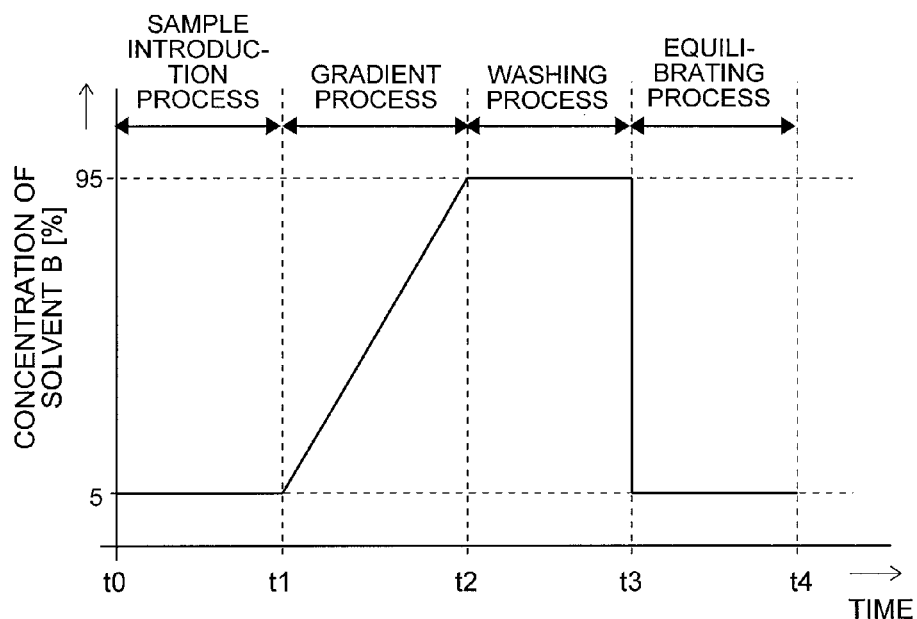
FIG. 3 is one example of the gradient profile.

As shown by the gradient profile in FIG. 3, the flow rates of the liquid-sending pumps $P_A$ and $P_B$ are initially controlled in such a manner that the ratio of solvent B is maintained at a low level and that of solvent A at a high level for a predetermined period of time after the injection of the sample (from t0 to t1: the sample introduction process). In this process, since the solvent used as solvent A has a low eluting power, the components in the sample are temporarily adsorbed on the column. Subsequently, the flow rates of the liquid-sending pumps $P_A$ and $P_B$ are changed with time so as to increase the ratio of solvent B (over a period of time from t1 to t2: the gradient process). In this process, since the solvent used as solvent B has a high eluting power, the components adsorbed on the column are sequentially eluted according to their degrees of polarity and introduced into the detecting unit 40.

The components introduced into the detecting unit 40 are sequentially detected by the detector 41, which produces detection signals corresponding to their concentrations. Those signals are converted into digital data and sent through the system controller 50 to the control system 60. In the control system 60, the received data are stored in the storage section 61 provided on a hard disk or similar storage device. Concurrently, the data processor 66 performs a predetermined process on the data to create a chromatogram, and displays it on the screen of the display unit 72. Subsequently, solvent B is supplied at a high concentration for a predetermined period of time (from t2 to t3) to wash the column (the washing process), after which the mobile phase is restored to the initial composition and supplied for a predetermined period of time (from t3 to t4) to equilibrate the column (the equilibrating process).

The periods of time to perform the sample introduction process, the gradient process, the washing process and the equilibrating process, as well as the composition of the mobile phase at the beginning of the gradient process, at the end of the gradient process and during the washing process, are hereinafter called the gradient condition.

Figure 2:
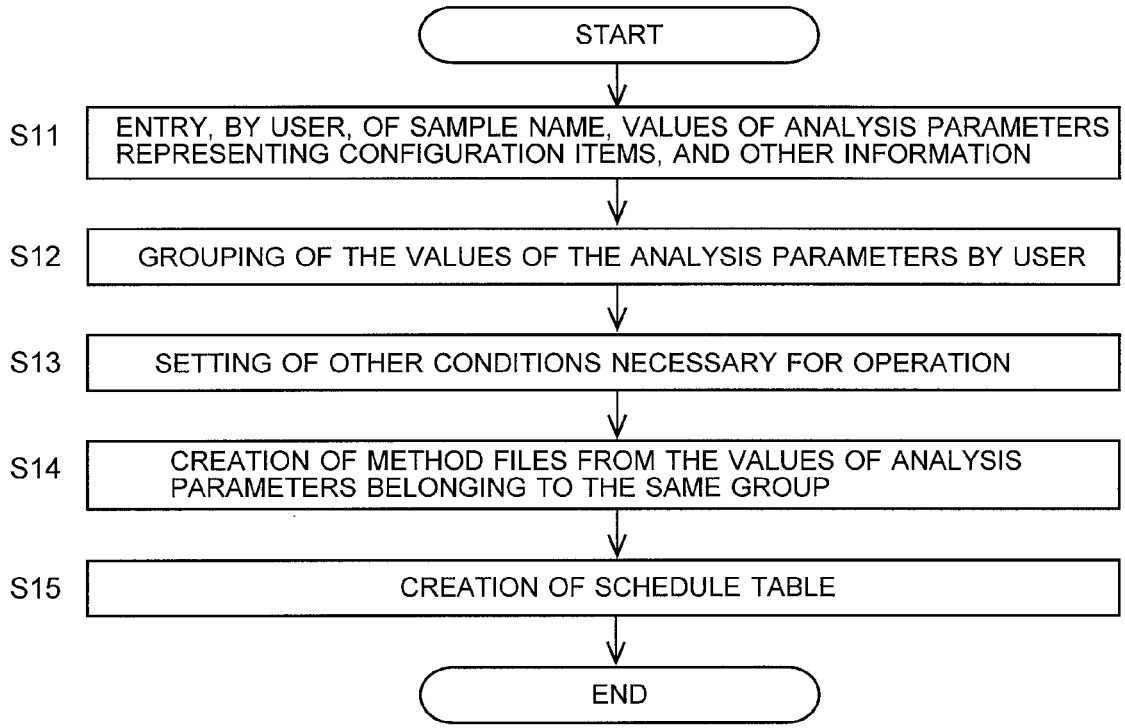
FIG. 2 is a flowchart showing an operation of the liquid chromatograph control system according to the embodiment.

As an operation characteristic of the liquid chromatograph control system of the present embodiment, an operation of creating method files each of which contains a different combination of the values of analysis parameters representing a plurality of configuration items is hereinafter described with reference to the flowchart of FIG. 2. As explained earlier, the method file is a file in which the values of parameters that specify operational conditions of each unit in the liquid chromatograph are stored. For example, this file contains the values of analysis parameters indicating the setting of various configuration items, such as the kind of mobile phase and the kind of column to be used in the analysis, the flow rate of a pump and the temperature of the column oven during the analysis.

Initially, by means of the operation unit 71, a user orders the analysis condition setter 62 to initiate the method scouting, whereupon a predetermined configuration screen (not shown) which shows the configuration items of each section that needs to be set is displayed on the screen of the display unit 72. On this configuration screen, the user enters the name of the sample to be analyzed, the amount of injection of the sample, as well as the values of the analysis parameters representing the configuration items which constitute the method file, such as a choice of the columns 32a-32f to be used (Step S11). Either a plurality of values or only one value may be entered for each analysis parameter. In the system of the present embodiment, since the mobile phase is composed of two kinds of solvents A and B, each of the solvents A and B is represented by one analysis parameter. For simplicity, it is hereinafter assumed that the two analysis parameters representing the solvents A and B only need to be set. Specifically, the user should enter the names of the solvents contained in the solvent containers 11a-11d as the values of the analysis parameter for solvent A and those of the solvents contained in the solvent containers 12a-12d as the values of the analysis parameter for solvent B.

Subsequently, the user performs the grouping of the values of the analysis parameters entered in Step S11, taking into account the appropriateness of each possible combination of one value of one analysis parameter and one value of another analysis parameter (Step S12). The "grouping" is the task in which the user determines whether or not the combination of one value of one analysis parameter and one value of another analysis parameter is appropriate, or whether or not it is meaningful, based on the physical and/or chemical properties of the substances, devices or other elements indicated by the values of the analysis parameters, and divides the values into groups in such a manner that any combination of the values belonging to the same group is appropriate or meaningful. The grouping can be expressed in an arbitrary way as long as the values belonging to each group can be identified. In the present embodiment, the grouping is made by entering a preset group number (or group name) based on the aforementioned physical and/or chemical properties. The set of group numbers thus entered correspond to the grouping information of the present invention.

The grouping may be performed for all the possible combinations of the values of the analysis parameters that can be set in the method file. In this case, if every analysis parameter has only one selectable value, or if there is only one value of one analysis parameter that can be set, then only the one value constitutes one group.

However, the grouping should preferably be performed for only such values of the analysis parameters that need to be examined as to the appropriateness for combination. For example, in the case where there are two or more analysis parameters each of which has a plurality of selectable values, the values of such analysis parameters are the "values of the analysis parameters that need to be examined as to the appropriateness for combination." If every analysis parameter has only one selectable value, or if there is only one value of one analysis parameter that can be set, the values of those analysis parameters can then be directly combined into one method file and there is no need to examine whether or not the combination is appropriate or meaningful.

Figure 4:
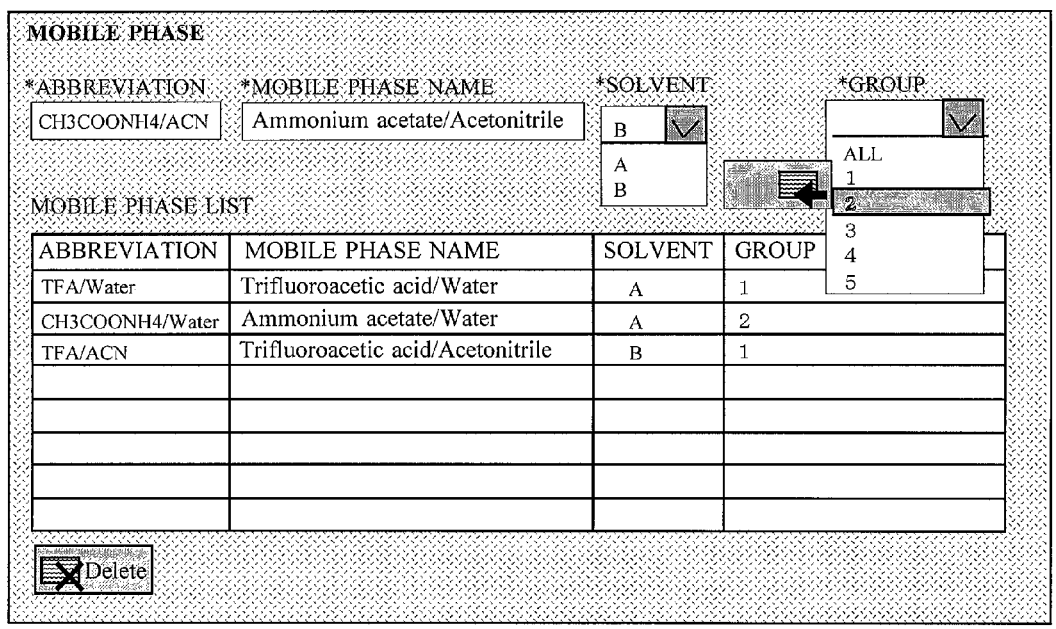
FIG. 4 schematically shows one example of the screen for allowing users to enter group names in the liquid chromatograph control system of the present embodiment.

In the present embodiment, as shown in FIG. 4, the group number is entered (i.e. the grouping is performed) for only such values of the analysis parameters that need to be examined as to the appropriateness for combination, i.e. for only the values of the two analysis parameters that respectively represent solvents A and B. In FIG. 4, the group number of each value of the analysis parameters is entered on the same screen as the configuration screen which is used for entering the values of the analysis parameters in Step S11. However, it is also possible to create a new screen which shows the values of the analysis parameters that can be selected and allows the user to enter the group number for each value.

A specific example of the grouping is hereinafter described. Suppose that two water-based solvents are set as the values of the analysis parameter of solvent A, one of which is composed of water with trifluoroacetic acid (TFA) as the additive (this solvent is hereinafter abbreviated as "TFA/Water") and the other is composed of water with ammonium acetate as the additive ("$CH_3COONH_4$/Water"), while two organic solvents are set as the values of the analysis parameter of solvent B, one of which is composed of acetonitrile with TFA as the additive ("TFA/ACN") and the other is composed of acetonitrile with ammonium acetate as the additive ("$CH_3COONH_4$/ACN"). As shown in FIG. 5A, there are four kinds of mobile phases (Nos. 1-4) that can be prepared by combining the two kinds of solvent A and the two kinds of solvent B.

However, a mobile phase composed of two solvents containing different kinds of additives is inappropriate for use in the analysis since the two different additives may cancel their respective effects or react with each other to produce a deposit. Among the four kinds of mobile phases shown in FIG. 5A, the mobile phases labelled as Nos. 2 and 3 are composed of such inappropriate combinations of the solvents. Taking this into account, the group numbers of the four solvents are set in such a manner that group number "1" is given to each solvent which contains TFA as the additive while group number "2" is given to each solvent which contains $CH_3COONH_4$ as the additive (FIG. 5B).

After the grouping is completed, other conditions necessary for the analysis are appropriately set by the analysis condition setter 62 (Step S13). In the present embodiment, since a gradient analysis is to be performed, a gradient profile as shown in FIG. 3 is created.

The task of Step S13 can be performed at any point in time between the entry and setting of the gradient condition in Step S11 and the creation of method files (which will be described later), and therefore, it may be performed before Step S12.

Subsequently, when the user performs a predetermined operation on the operation unit 71 to order the method file creator 63 to create a method file, such values of the analysis parameters that belong to the same group are extracted (selected) from the values of all the analysis parameters and compiled into a method file, which is stored in the storage section 61 (Step S14).

In the present embodiment, one method file in which the combination of one kind of solvent A and one kind of solvent B having the same group number is designated as the mobile phase is automatically created for each group. Specifically, there are only two choices of the mobile phase: the combination of "TFA/Water" and "TFA/ACN" having group number "1" (No. 1 in FIG. 5A) and the combination of "$CH_3COONH_4$/Water" and "$CH_3COONH_4$/ACN" having group number "2" (No. 4 in FIG. 5A). Thus, a total of two method files are created (FIG. 6A), each file containing one of the two mobile phases combined with the values of the analysis parameters representing the other configuration items each of which has only one selectable value.

Subsequently, the user performs a predetermined operation on the operation unit 71, whereupon the schedule table creator 64 creates a schedule table, with the names of the method files created in Step S14 written in the corresponding column (Step S15). In the present example, a schedule table which holds two rows of the information necessary for performing the analysis shown in FIG. 7 is created and displayed on the screen of the display unit 72. After that, when a command for initiating the analysis is entered, a preliminary analysis of the samples is performed according to the created schedule table.

If the conventional method is used, the method files are automatically created for all kinds of mobile phases that can be prepared by combining the two kinds of solvent A and the two kinds of solvent B, so that a total of four method files will be created (FIG. 6B), which does not only include the two aforementioned method files but also two other method files in which the combinations of two solvents containing different additives (Nos. 2 and 3 in FIG. 5A) are designated as the mobile phase. As a result, a schedule table is created from the four method files and the preliminary analysis is performed according to this schedule table. As already stated, it is not preferable to perform an analysis using a mobile phase composed of two solvents containing different additives. Such an analysis is a waste of time, sample and solvents.

By contrast, in the present embodiment, the method files are created for only such combinations of the values of the analysis parameters that belong to the same group and can be appropriately combined, and no useless preliminary analysis is performed. Accordingly, the period of time for the analysis can be shortened, and the wasting of sample and solvents can be prevented.

It should be noted that the present invention is not limited to the embodiment described thus far by means of the specific examples. It is possible to change or modify the previous embodiment within the spirit and scope of the present invention. For example, the following variations are possible.

In the previous embodiment, the grouping of the values of the analysis parameters representing solvents A and B was performed based on the kind of additive. In some cases, the solvents should be grouped by the concentration of the additive. For example, suppose that three solvents which respectively contain formic acid as the additive at concentrations of 0%, 0.01% and 0.1% are available as solvent A, and three other solvents which also respectively contain formic acid as the additive at concentrations of 0%, 0.01% and 0.1% are available as solvent B. In this case, combining solvents A and B having different formic-acid concentrations is not preferable since the formic-acid concentration of the resulting mobile phase changes with time. Accordingly, the grouping should be performed in such a manner that the solvents having the same formic-acid concentration will be included in the same group.

In the case where an analysis parameter representing the kind of column also has a plurality of selectable values, it is possible to perform the grouping taking into account the appropriateness of the combination of the kind of column and the kind of mobile phase.

One value of an analysis parameter can belong to two or more groups. For example, in the case where an analysis parameter representing the kind of column also has a plurality of selectable values ("C1" and "C2") in addition to solvents A and B described in the previous embodiment, if the columns C1 and C2 can be used in both an analysis using the mobile phase composed of the solvents of group number "1" and an analysis using the mobile phase composed of the solvents of group number "2", both group numbers "1" and "2" should be assigned to each of the columns C1 and C2. In this example, a total of four method files which respectively contain the four different combinations of the values of solvent A, solvent B and the column will be created.

Examples of the criteria for determining the appropriateness of the combination of the solvents used as the mobile phase include the kinds of solvents (e.g. water-based or organic), the pH values of the solvents, and the chemical properties of the solvents (e.g. basic or acidic).

REFERENCE SIGNS LIST

10 . . . Liquid-Sending Unit
11a-11d, 12a-12d . . . Solvent Container
$P_A$, $P_B$ . . . Liquid-Sending Pump
15, 16 . . . Solvent-Switching Valve
17 . . . Gradient Mixer
20 . . . Auto-Sampler
30 . . . Column Oven
32a-32f . . . Column
40 . . . Detecting Unit
41 . . . Detector
50 . . . System Controller
60 . . . Control System
61 . . . Storage Section
62 . . . Analysis Condition Setter
63 . . . Method File Creator
64 . . . Schedule Table Creator
65 . . . Analysis Controller
66 . . . Data Processor
71 . . . Operation Unit
72 . . . Display Unit

The invention claimed is:

1. A liquid chromatograph system; comprising:
a liquid chromatograph including
a liquid sending device for drawing solvents,
a sampler configured to inject a sample and receive the solvents;
a column oven including columns configured to receive the sample and solvents from the sampler, and
a detector for detecting components of the sample; and
a control system for controlling an operation of the liquid chromatograph according to a method file describing analysis parameters of a plurality of configuration items which determine operational conditions of the liquid chromatograph, wherein the plurality of configuration items include at least one configuration item for which a plurality of analysis parameters are set, the at least one configuration item determining an operational condition of the liquid sending device, the sampler, or the column oven, the control system comprising:
a computer configured to
display selectable values of the analysis parameters of the at least one configuration item on a condition-setting screen;
classify a first plurality of the displayed selectable values of the analysis parameters into a first group of a plurality of groups based on user input of a first code which corresponds to the first group, the first code being one code of a plurality of codes, each of the plurality of codes comprising a preset number or name, the first code being input by the user on the display for each of the at least one configuration item for classifying one value of one analysis parameter and one value of another analysis parameter in the first group;
classify a second plurality of the displayed selectable values of the analysis parameters into a second group of the plurality of groups based on user input of a second code which corresponds to the second group, the second code being another code of the plurality of codes, the second code being input by the user on the display for each of the at least one configuration item for classifying one value of one analysis parameter and one value of another analysis parameter in the second group;

extract a value of each of the analysis parameters having the same first code for each of the plurality of the configuration items, create a method file by combining the extracted values, the method file including values of parameters of the at least one configuration items for the liquid sending device, the sampler, or the column oven; and control the operation of the liquid chromatograph according to the method file.

2. The liquid chromatograph system according to claim 1, wherein the configuration items include a plurality of kinds of solvents which compose a mobile phase in an analysis.

3. The liquid chromatograph system according to claim 2, wherein the configuration items further include kinds of the columns.

4. The liquid chromatograph system according to claim 1, wherein the computer is further configured to extract a value of each of the analysis parameters having the second code for each of the plurality of the configuration items, and create a method file for the second code by combining the extracted values, the method file for the second code including values of parameters of the at least one configuration items for the liquid sending device, the sampler, or the column oven.

* * * * *